United States Patent [19]

Senturia

[11] 4,236,121
[45] Nov. 25, 1980

[54] OSCILLATORS INCLUDING CHARGE-FLOW TRANSISTOR LOGIC ELEMENTS

[75] Inventor: Stephen D. Senturia, Cambridge, Mass.

[73] Assignee: Massachusetts Institute of Technology, Cambridge, Mass.

[21] Appl. No.: 893,552

[22] Filed: Apr. 5, 1978

[51] Int. Cl.² .................. H03K 3/282; H03K 3/353
[52] U.S. Cl. ................................. 331/57; 307/205; 307/308; 331/65; 331/111; 331/113 R; 331/135; 357/23; 357/25
[58] Field of Search ........... 331/65, 66, 108 C, 108 D, 331/108 R, 111, 143, 113 R, 57, 135; 307/304, 308, 205; 357/23, 25

[56] References Cited

U.S. PATENT DOCUMENTS

| | | | |
|---|---|---|---|
| 3,509,383 | 4/1970 | Sangster | 331/65 X |
| 4,110,704 | 8/1978 | Irwin et al. | 331/111 X |

OTHER PUBLICATIONS

Senturia et al., "The Charge-Flow Transistor: A new MOS Device", Applied Physics Letters, vol. 30, No. 2, Jan. 15, 1977, pp. 106–108.

Huang, "Light Sensitive Oscillator", IBM Technical Disclosure Bulletin, vol. 8, No. 4, Sep. 1965, p. 653.

Primary Examiner—Siegfried H. Grimm
Attorney, Agent, or Firm—Arthur A. Smith, Jr.; Robert Shaw

[57] ABSTRACT

Oscillators that include charge-flow transistor logic elements, each logic element including a charge-flow transistor and a load element, in combination. The charge-flow transistors have TURN-ON times $t_{on}$ and TURN-OFF times $t_{off}$ that can be very different from one another (e.g., $t_{on}$ can range from milliseconds to hundreds of seconds; whereas in the charge-flow transistors shown herein $t_{off}$ is typically less than one microsecond). The magnitude of $t_{on}$ is sensitive to the environment; hence, the period of oscillation can be used as a measure of an environmental condition.

48 Claims, 22 Drawing Figures

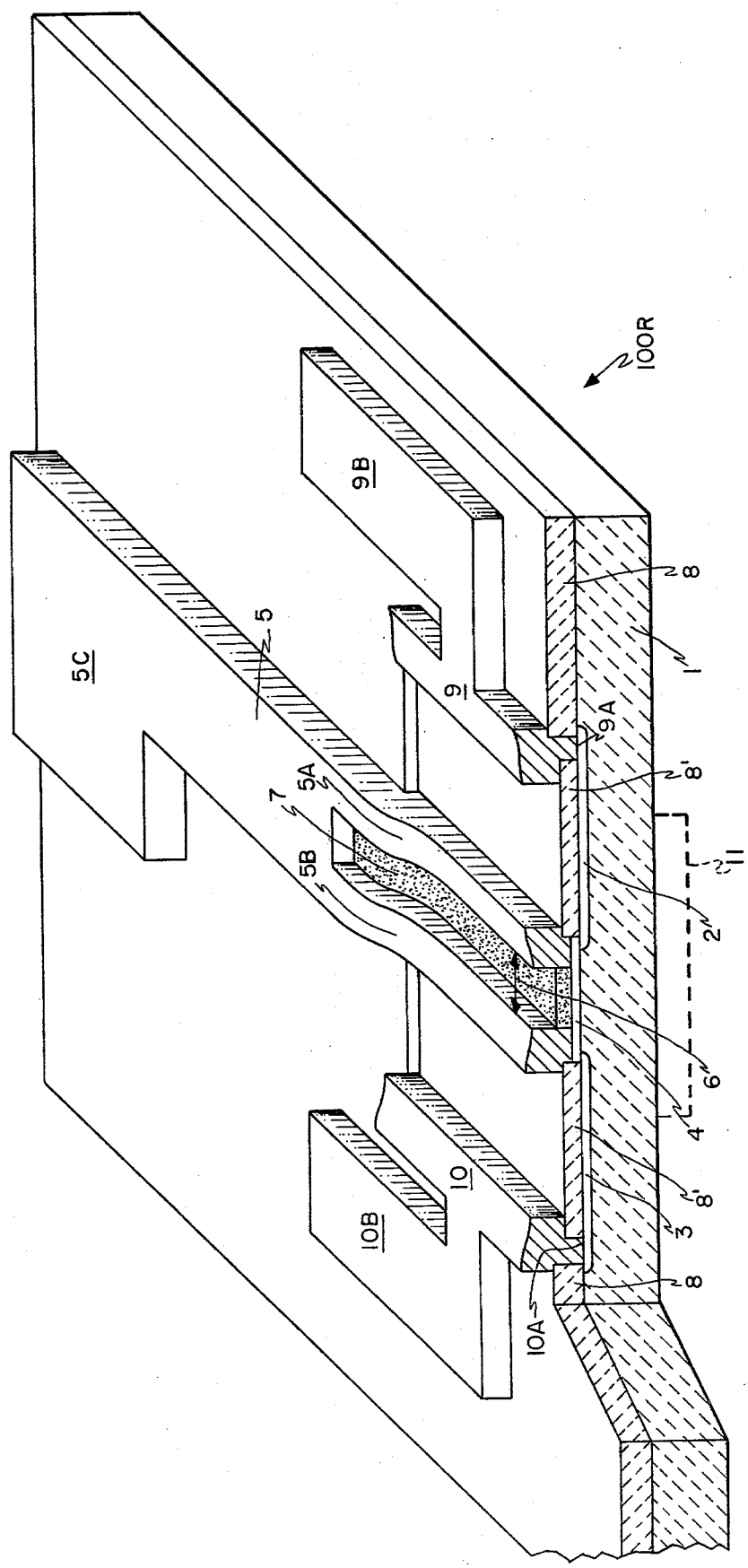

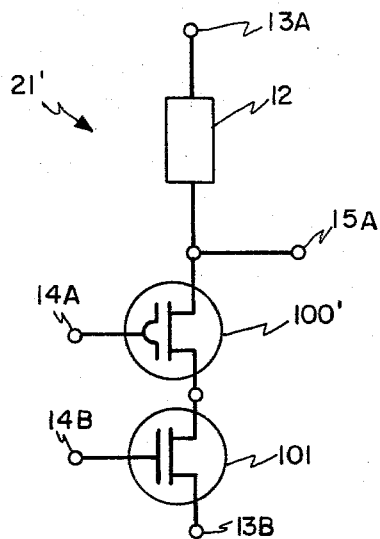
FIG. 5A
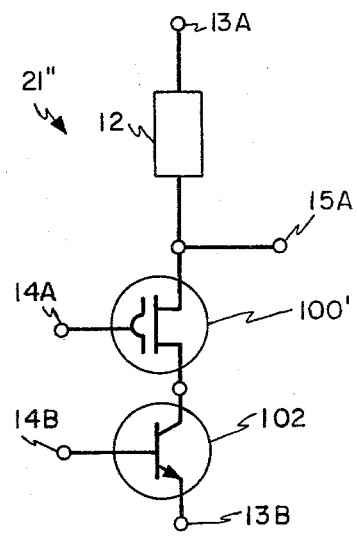
FIG. 5B
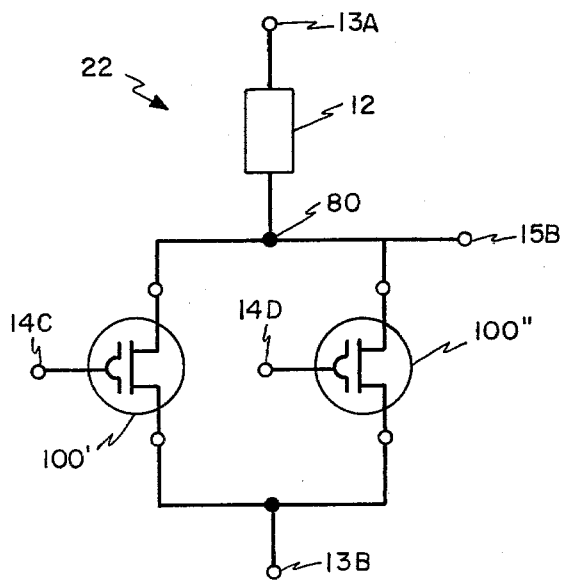
FIG. 6
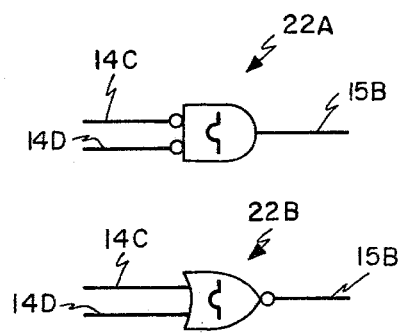
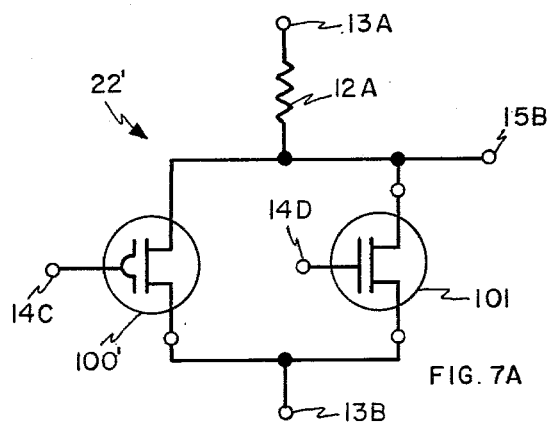
FIG. 7A
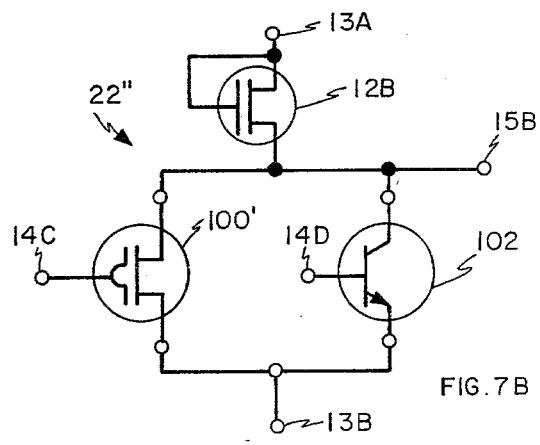
FIG. 7B

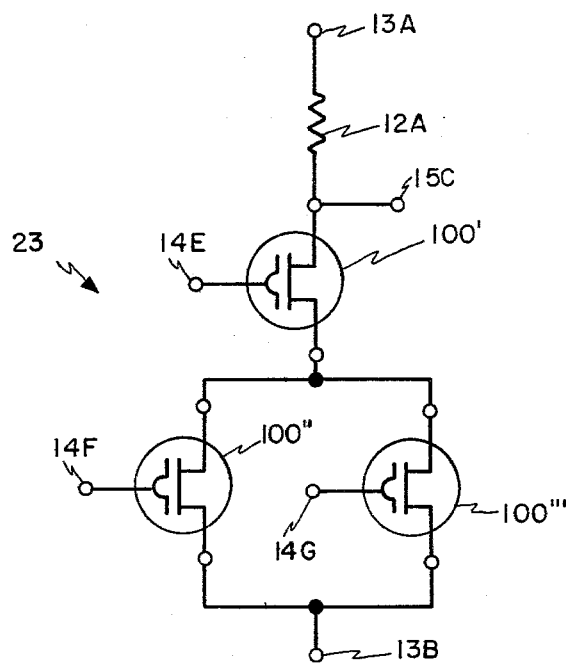
FIG. 8
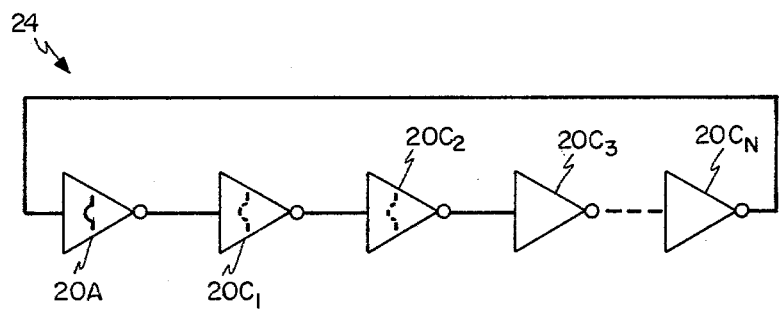
FIG. 9
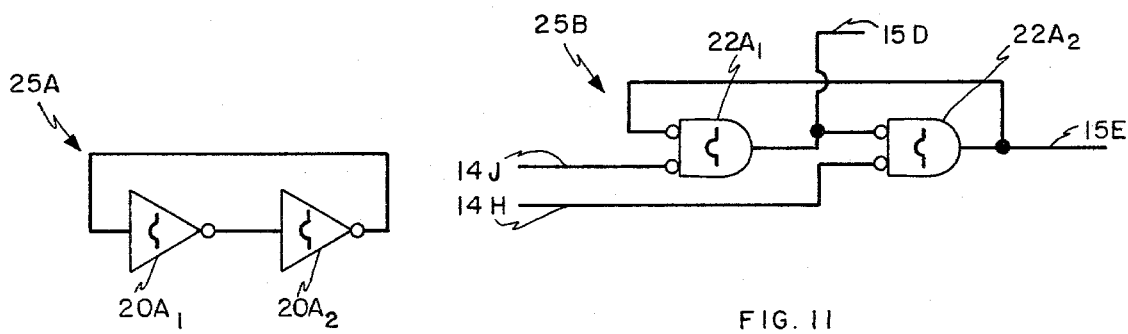
FIG. 10
FIG. 11

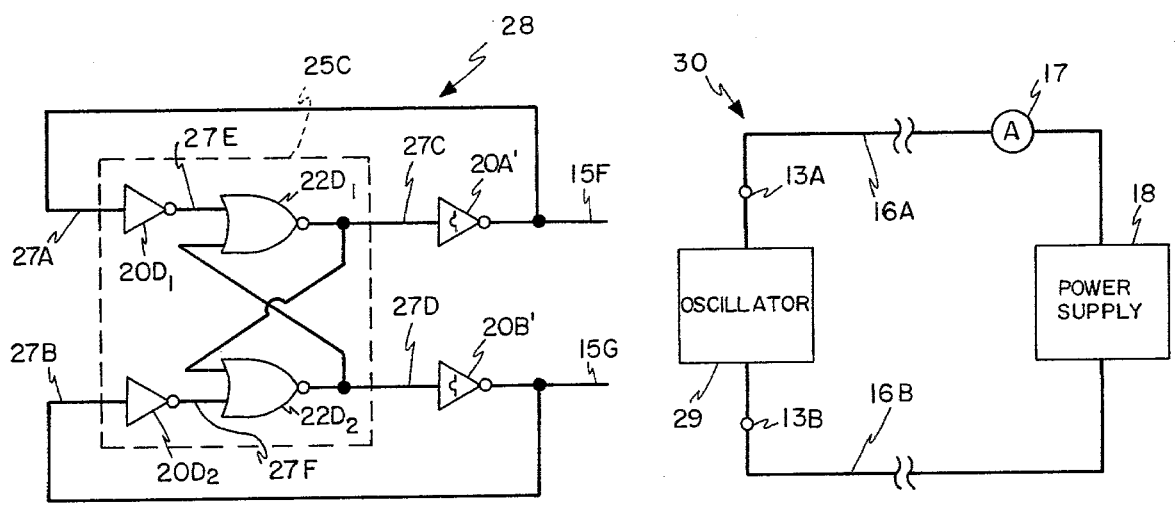
FIG. 12
FIG. 14
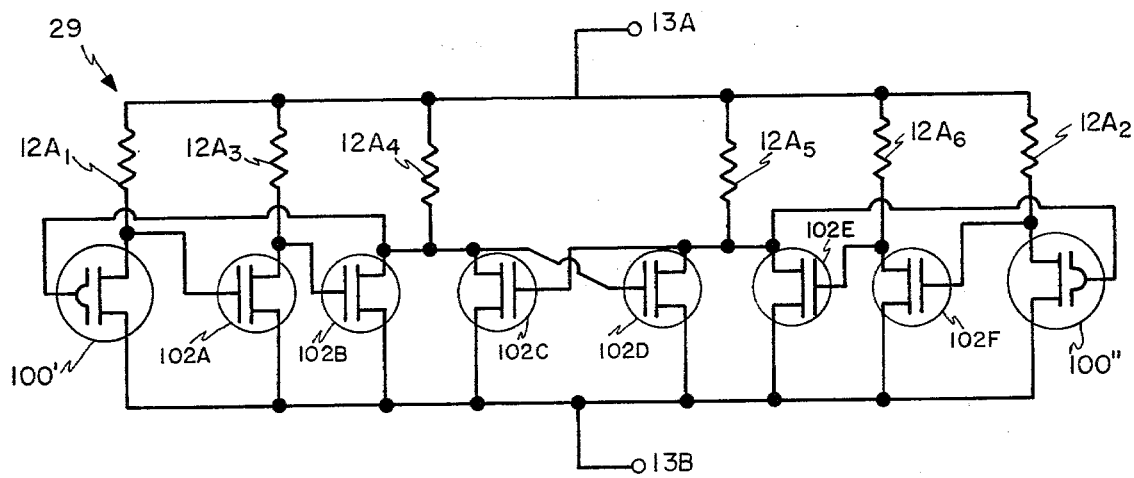
FIG. 13
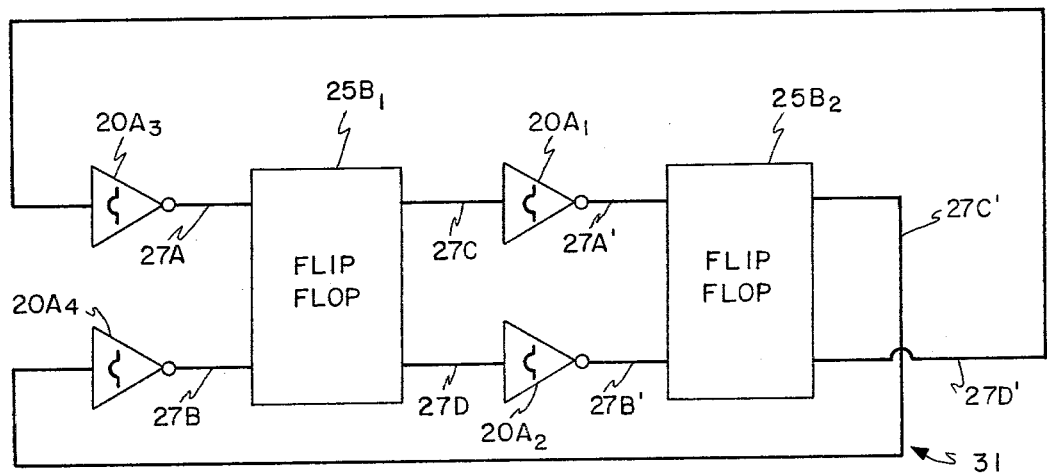
FIG. 15

OSCILLATORS INCLUDING CHARGE-FLOW TRANSISTOR LOGIC ELEMENTS

The government has rights in this invention pursuant to Contract No. N00014-77-C-0361 awarded by the Office of Naval Research a department of the United States Navy.

The present invention relates to logic elements and to systems constructed of said elements, which logic elements transistors.

Attention is called to an application for Letters Patent, Ser. No. 790,631, filed Apr. 25, 1977 by the present inventor (now U.S. Pat. No. 4,158,807); said application goes into exhaustive detail in describing charge-flow transistors; such transistors, among other things, have a gapped gate electrode with a thin-film material in the gap. The application, as well as the prior art therein cited, may be used by way of background. Attention is also called to a further application for Letters Patent, Ser. No. 853,059, filed Nov. 21, 1977 by the present inventor. Both applications are assigned to the Massachusetts Institute of Technology, Cambridge, Massachusetts, the assignee herein.

The use of charge-flow transistors in logic elements and logic systems stems from recognition by the present inventor that because of the structure of such charge-flow transistors, and unlike conventional field-effect transistors, the charge-flow transistors have TURN-ON times ($t_{on}$ herein) and TURN-OFF times ($t_{off}$ herein) that can be very different from one another. $t_{on}$ is limited by charge-flow processes in the thin-film material, which are typically much slower than corresponding processes in metals and semiconductors; hence $t_{on}$ is relatively long, can be variable, and can carry information (e.g., due to the change in thin-film conduction produced by the presence or absence of smoke in the environment in which the transistor is located). On the other hand, $t_{off}$ depends only on the relatively rapid conduction of charge in semiconductors and metals, and hence is relatively short, equivalent to gate propagation delays in conventional MOS logic circuits. This asymmetry between $t_{on}$ and $t_{off}$ leads to the possibility of new types of logic elements and systems of logic elements, both for the processing of conventional digital signals and for new signal-processing functions.

Accordingly, it is an object of the present invention to provide logic elements such as inverters, NOR-gates, and NAND gates, that include, as a building block or unit thereof, a charge-flow transistor, these logic elements having new combinational-logic properties because of the asymmetry or discrepancy between $t_{on}$ and $t_{off}$ of the charge-flow transistor.

Another object is to provide logic systems that are formed of a plurality of such logic elements.

Still another object is to provide memory elements formed of a plurality of such logic elements.

A still further object is to provide oscillator circuits that include such logic elements, these oscillator circuits exhibiting periodic waveforms with periods and/or duty cycles that depend primarily on $t_{on}$ of the charge-flow transistors in the logic elements, thereby permitting convenient determination of $t_{on}$ and its variation as a function of properties of the environment in which the charge-flow transistor is located.

In sensing applications, such as the presence of smoke or humidity, it is common industrial practice to locate the sensor element at a considerable distance from the instrument or monitor that records and/or interprets the data from the sensor, communications being provided by a single pair of wires. An important property of a sensor, therefore, is its suitability for remote two-wire operation.

Accordingly, a still further object of the present invention is to provide oscillator circuits that can be used in sensing applications and that are configured for remote use, connected to a monitor by only a single pair of wires.

It has been discovered by the inventor that because of variations between bulk and surface conductance in some thin-film materials appropriate for use in charge-flow transistors, a charge-storage phenomenon in the thin film occurs, leading to a variation of $t_{on}$ that depends on the average drive signal applied to the gate of a charge-flow transistor. One result of this charge-storage phenomenon is that oscillators that include charge-flow transistor logic elements and that are designed to have periods and/or duty cycles that depend primarily on $t_{on}$ can exhibit frequency drift which impairs the usefulness of the oscillator circuits.

Accordingly, a still further object of the present invention is to provide oscillator circuits that are stabilized against frequency drift produced by charge-storage in the thin-film material of the charge-flow transistor.

It has been found for present purposes that charge-flow transistors can be made compatible with MOS logic and can even be fabricated as part of the same integrated circuit; still another object, therefore, is to provide charge-flow transistors in combination with MOS logic and as part of the same integrated circuit as the MOS logic.

These and still further objects are addressed hereinafter.

The foregoing objects are achieved, generally, in a logic element that includes the combination of a charge-flow transistor and a load element, the load element being connected to the source region or the drain region of the charge-flow transistor. The logic element, so formed, may be combined with other logic elements to form logic systems and oscillators.

The invention is hereinafter described with reference to the accompanying drawing in which:

FIG. 2 is an isometric view, on an enlarged scale, partly cutaway and partly diagrammatic in form, of a charge-flow transistor;

FIGS. 5A and 5B are schematic representations of logic elements (i.e., two-input NAND-gates) that each include a charge flow transistor in combination with a conventional transistor;

FIG. 6 is a schematic representation of a logic element (i.e., a two-input NOR-gate) that includes two charge-flow transistors, and two logic symbols therefor;

FIGS. 7A and 7B are schematic representations of logic elements (i.e., two-input NOR-gates) each of which includes a charge-flow transistor in combination with a conventional transistor and each of which shows a specific form for the load element;

FIG. 8 is a schematic of a complex logic unit formed of a NAND-gate and a NOR-gate;

FIG. 9 is a schematic representation showing a plurality of logic elements, as shown in FIG. 3, in the form of a ring oscillator;

FIG. 10 is a schematic representation of a memory element consisting of two logic elements as shown in FIG. 3;

FIG. 11 is a schematic representation of a memory element consisting of a plurality of logic elements as shown in FIG. 6;

FIG. 12 is a schematic representation of an oscillator circuit comprising a flip-flop memory element and two logic elements as shown in FIG. 3;

FIG. 13 is an explicit circuit diagram that corresponds to the oscillator represented in FIG. 12;

FIG. 14 is a schematic representation of a two-wire remote sensing circuit that includes an oscillator of the present invention, a power supply, and a current monitor;

FIG. 15 is a schematic representation of an oscillator formed of four logic elements as shown in FIG. 3 and two flip-flops;

Figure 1:
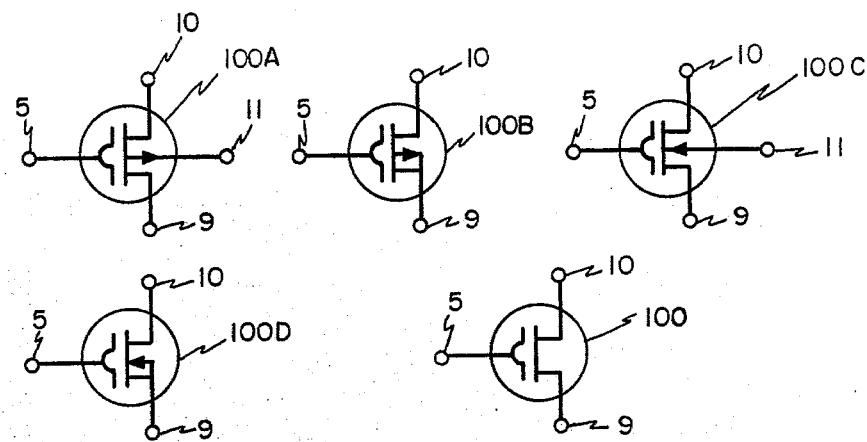
FIG. 1 shows symbols for four configurations of charge-flow transistors and a fifth generic symbol, used to represent any one of the four configurations, these symbols serving as a basis for the schematics of logic elements in later figures.

In order to establish a basis for the discussion later, there first follows a description of a charge-flow transistor with reference to FIG. 2 wherein the charge-flow transistor shown is labeled 100R. The charge-flow transistor has a substrate 1, a source region 2, a drain region 3, a gate insulator 4, and a gapped gate electrode 5 comprising fingers 5A and 5B with a gap 6 between the fingers (throughout this specification an attempt is made to apply the same or similar labels to the various elements that provide the same or similar functions) and contact pad 5C. A thin-film material 7 having some electrical conductance, as hereinafter discussed, is disposed in the gap 6. As known to workers in the art to which the present disclosure is directed, electrical connection must be made to the source region 2 and the drain region 3; that connection can be made by electrical contacts 9 and 10, respectively. Hereinafter the terms "source" and "drain" designate connections respectively to the source region 2 and the drain region 3 and the numerals 9 and 10 in the schematics herein denote such connection which is conventionally made by contacts as shown in FIG. 2. Electrical contact to the source region 2 in FIG. 2 is made at 9A and electrical contact to the drain region 3 is made at 10A. The contact 9 has a contact pad 9B and the contact 10 has a contact pad 10B. Insulating layers 8 and 8' in FIG. 3 serve to insulate the contacts 9 and 10 and the gate electrode 5 from the substrate 1 and from each other. The charge-flow transistor 100R may have a substrate contact 11.

The thin-film material 7 is ~100 Å to 10,000 Å thick; the width of the gap (and, thus, the film 7) is ~0.1 to 1.5 mils and its length is typically ~1 to 10 mils. The electrical conductance of the thin-film material expressed as a sheet conductance is typically greater than about $10^{-17}$ (ohms/square)$^{-1}$ with an upper limit at about $10^{-6}$ (ohms/square)$^{-1}$. Materials that are suitable for use in the gap 6 of the charge-flow transistors include organic polymers, metal oxides, oxide glasses, films of adsorbed moisture, metallo-organic compounds, chalcogenide glasses, and other amorphous inorganic semiconductors.

The operation of a charge-flow transistor is now described, for the particular case of an enhancement-mode, p-channel transistor (other cases are fully described in the application for Letters Patent Ser. No. 790,631). In this case, the substrate 1 is an n-type semiconductor, and the source 2 and drain 3 are p-type regions in the substrate. In order for conduction to take place between source and drain, i.e., to TURN-ON the transistor, it is necessary to convert that region of the substrate surface beneath gate insulator 4 from n-type to p-type by application of a suitable voltage between gate electrode 5 and substrate 1 (this can also be accomplished by application of a suitable voltage between the gate electrode 5 and the source 2 or the drain 3). For the present p-channel case, the gate-to-substrate voltage is made negative. TURN-ON proceeds in two steps. First, beneath the metallic fingers 5A and 5B of gate electrode 5, conversion of the substrate surface from n-type to p-type (a process called inversion) takes place very rapidly, typical times being less than 1 microsecond. The second step is much slower, because charge (negative charge in this case) must flow in the thin-film 7 from fingers 5A and 5B toward the center of the gap 6. The speed of this process depends on the sheet conductance of the thin film. As negative charge flows in the thin film, equal and opposite positive charge is induced in the substrate beneath the gate gap 6. When sufficient negative charge has flowed, the substrate surface beneath the gap 6 becomes p-type and conducts, completing the conduction path between the source 2 and the drain 3. Typical times for this turn-on process (i.e., for the time $t_{on}$) range from milliseconds for sheet conductance of about $10^{-6}$ (ohms/square)$^{-1}$ to hundreds of seconds for sheet conductance of about $10^{-17}$ (ohms/square)$^{-1}$. When the gate-to-substrate voltage is removed, the substrate region beneath the fingers 5A and 5B returns to n-type very quickly, breaking the conduction path between the source 2 and the drain 3. This TURN-OFF process occurs within a time $t_{off}$ that is typically less than one microsecond, on the order of gate-propagation delays in conventional MOS logic circuits. Hence, the structure of the charge-flow transistor causes $t_{on}$ and $t_{off}$ to be very different from one another. Further, in cases where the thin-film sheet conductance depends on a property of the environment in which the transistor is located, it is evident from this explanation that $t_{on}$ will vary with that property, and hence serves to sense or measure that property, but that $t_{off}$ will not vary with that property.

Logic elements typically are circuits that, when connected to a suitable power supply, provide that input signals (e.g., voltages) in one of two well-defined voltage ranges produce output signals (e.g., voltages) in one of those same two voltage ranges, thereby making it possible to connect the output of one logic element to serve as an input to a second logic element. The present invention relates to new logic elements that employ charge-flow transistors and load elements. Some of the logic elements formed using charge-flow transistors and load elements are discussed below.

In the schematic representations of those logic elements, the charge-flow transistor included may be of the type represented by symbols shown at 100A, 100B, 100C and 100D in FIG. 1 representing respectively a p-channel, charge-flow transistor with a separate substrate contact (i.e., the contact 11 in FIG. 2), a p-channel charge-flow transistor with its substrate contact connected to the source thereof, an n-channel charge-flow transistor with a separate substrate contact, and an n-channel charge-flow transistor with its substrate connected to the source thereof. The symbol 100 is a generic symbol that will be used in subsequent diagrams to represent a charge-flow transistor of types 100A, 100B, 100C, or 100D, and it can also represent a charge-flow transistor without a substrate connection. In FIG. 1 the numeral 5 designates the gate or gate electrode, the numeral 9 designates the source (or connection to the source region 2 in FIG. 2) and the numeral 10 designates the drain (or connection to the drain region 3 in FIG. 2). Various logic elements are now taken up: in the discussion, the numerals 13A and 13B are used to represent terminals of the logic element to which a suitable power supply is to be connected; the numeral 14 and variations thereof are used to represent an input to the logic element; and the numeral 15 and variations thereof are used to represent an output from the logic element.

Figure 3:
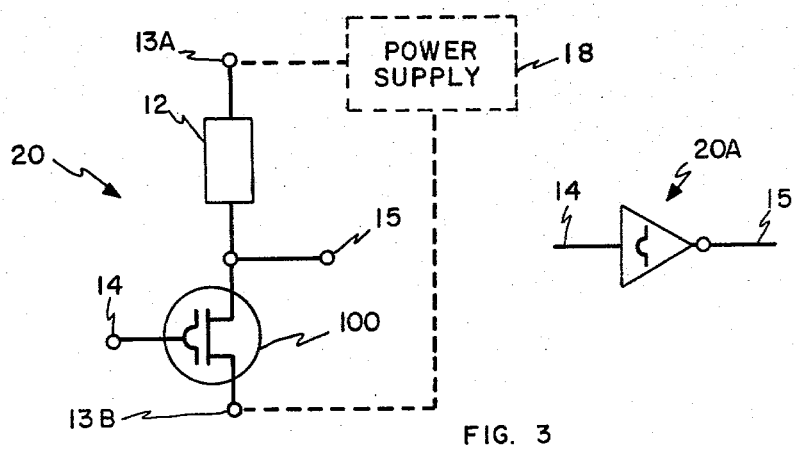
FIG. 3 is a schematic representation of a logic element (i.e., an inverter) that includes a charge flow transistor connected to a power supply, and a logic symbol therefor.

Turning now to FIG. 3, there is shown a power supply 18 connected at terminals 13A and 13B to a logic element 20 (which is an inverter) that consists of a load element 12 (i.e., an impedance element such as a resistance, for example) serially connected with a charge-flow transistor which is again designated 100 and which may take any of the forms 100A–100D in FIG. 1. The inverter 20 is symbolically represented by a logic symbol marked 20A in FIG. 3; the input 14 of the inverter 20A is the gate of the transistor 100 in FIG. 3, the load element 12 is connected to either the source or the drain of the charge-flow transistor 100, and the output 15 is at the common connection between the charge-flow transistor 100 and the load element 12.

Operation of the inverter 20 is now described. When the transistor 100 is OFF (no conduction between source and drain), the voltage between the output 15 and the terminal 13B is equal to the power supply voltage from power supply 18, called a HI voltage, because there is no current in the load element 12. This OFF state is achieved by connecting the input 14 to a voltage that is too small to achieve transistor TURN-ON, this voltage being called a LO voltage. That is, a LO input voltage yields a HI output voltage. In the other state, in which the transistor 100 is ON, the voltage between the output 15 and the terminal 13B is smaller than the supply voltage because the current in the load element 12 produces a voltage drop between the terminal 13A and the output 15. This ON state is achieved by connecting the input 14 to a voltage that is large enough to achieve TURN-ON. If the supply voltage is large enough to achieve TURN-ON and the ON state output voltage is itself too small to achieve TURN-ON, then an equivalent description of the ON state is that a HI input yields a LO output. It is necessary to select a specific power supply voltage and specific load element 12 to achieve the output-to-input compatibility in both HI and LO voltage ranges desirable for logic elements, the HI and LO ranges depending on the threshold voltage of the transistor 100 (i.e., the minimum voltage (in magnitude) needed to achieve TURN ON) and on the amount of current conducted by the transistor 100 when ON. (In one embodiment of the logic element 20, the transistor 100 was a p-type enhancement mode transistor incorporating poly(p-aminophenylacetylene) as thin-film material 7 and having a 16-volt threshold voltage and an ON current of ∼15 microamperes when used with a 25-volt power supply and a load element 12 comprising a ∼500 kΩ resistor.) The inverter thus formed differs from a conventional inverter in that the speed of operation depends markedly on the starting state. If the transistor 100 is OFF and a HI voltage is applied to the input 14, the output 15 becomes LO only after a time $t_{on}$. Conversely, if the transistor 100 is ON and a LO voltage is applied to input 14, the output 15 becomes HI very quickly, i.e., after time $t_{off}$. Pluralities of such logic element (i.e., inverters) have been successfully used, with the output of one connected to the input of another, to form logic systems, as described later.

Figure 4:
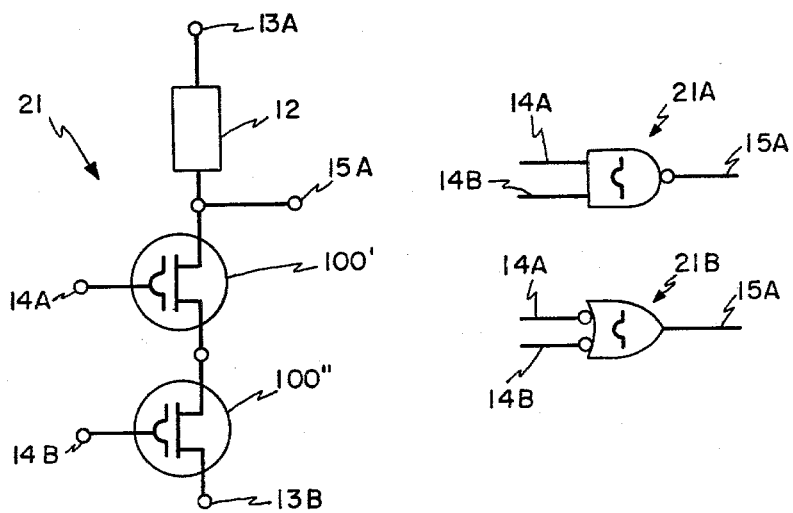
FIG. 4 is a schematic representation of a logic element (i.e., a two-input NAND-gate) that includes two charge-flow transistors, and two logic symbols therefor.

A two-input NAND-gate 21 in FIG. 4 is formed of a load element 12 serially connected with a charge-flow transistor pair consisting of a first charge-flow transistor 100' (like the transistor 100) and a second similar charge-flow transistor 100" connected in series with the first charge-flow transistor; that is, the drain of one transistor is connected to the source of the other transistor. The NAND-gate 21 is symbolically represented by the symbols 21A and 21B in FIG. 4. The inputs to the NAND-gates 21A and 21B are marked 14A and 14B and the output of each is marked 15A. The inputs 14A and 14B are the gates of the charge-flow transistors 100' and 100", respectively, and the output 15A is the common connection between the load element 12 and the first transistor 100' in FIG. 4.

Operation of the NAND-gate is now described, assuming connection to a suitably chosen power supply as in FIG. 3. The output voltage at 15A will be in the HI range unless both the transistors 100' and 100" are in the ON state. This is the conventional NAND function. However, because of the TURN ON times of the transistors 100' and 100", the output 15A makes a HI to LO transition only after the greater of the two times $t_{on}$ of the transistors 100' and 100". Thus the NAND-gate 21, in addition to the conventional NAND function, has the property of selecting the longer of two $t_{on}$ times, either or both of which might depend on properties of the environment.

FIGS. 5A and 5B show NAND-gates 21' and 21", respectively, wherein the second transistor 100" of FIG. 4 is replaced respectively by a conventional FET 101 and a bipolar junction transistor 102. In these circuits, the conventional transistor can serve to control or enable the propagation of signals through the charge-flow transistor; or, equivalently, the charge-flow transistor, which has variable $t_{on}$, can be used as a time-delayed enable for propagation of conventional logic signals through the conventional transistor.

The logic element shown at 22 in FIG. 6 is a two-input NOR-gate consisting of a load element 12 connected in series with a pair of parallel-connected charge-flow transistors 100' and 100". The NOR-gate 22 is symbolically represented by 22A and 22B with inputs 14C and 14D and output 15B. The inputs 14C and 14D in FIG. 6 are the gates of the parallel-connected charge-flow transistors 100' and 100" and the output 15B is the common connection shown at 80 in FIG. 6 between the load element 12 and the parallel-connected charge-flow transistors 100' and 100" therein.

Operation of the NOR-gate 22 is similar to that of the NAND-gate 21, except that the output 15B is LO whenever either transistor 100' or 100" is ON. Hence, the NOR-gate 22 performs the conventional NOR function and, in additon, has the property of selecting the shorter of the two $t_{on}$ times of the transistors 100' and 100" in FIG. 6.

FIGS. 7A and 7B show NOR-gates 22' and 22", respectively, wherein the second transistor 100" of FIG. 6 is replaced respectively by a conventional FET 101 and a bipolar junction transistor 102. In addition, FIG. 7A shows a specific embodiment of the load element 12 of FIG. 6 as a resistor 12A, and FIG. 7B shows a second embodiment of the load element 12 of FIG. 6 as a load FET 12B. Both types of load elements are widely used as load elements in conventional MOS logic elements and can be easily fabricated on a nearby portion of the same piece of semiconductor used for the substrate of the transistor 100'.

The logic element designated 23 in FIG. 8 is a complex element consisting of a load element resistor 12A serially connected with a charge-flow transistor 100' and the two are connected with parallel-connected charge-flow transistors 100" and 100'''. Inputs 14E, 14F and 14G are the gates of the transistors 100', 100" and 100''', respectively, and the output 15C thereof is the common connection between the transistor 100' and the resistor 12A.

The element 23 performs the complex logic function described as follows: Output 15C is LO only when 14E is HI and either 14F or 14G or both are HI. Similar combinational logic circuits are in widespread use. However, in the case of the charge-flow transistor logic, the circuit also performs the function of selecting the longer of, first, $t_{on}$ for the transistor 100' in FIG. 8 and, second, whichever is shorter of the $t_{on}$ times for the transistors 100" and 100'''. That is, if HI signals were simultaneously applied to the inputs 14E, 14F and 14G, the time before the output 15C goes LO depends, as described above, on the three $t_{on}$ times of the transistors 100', 100", and 100'''. If one (or more) of these $t_{on}$ times depends on a property (or several properties) of the environment, circuits such as 23 can be used to process data on the environment as reflected in the various $t_{on}$ times.

Memory elements can be formed of a plurality of charge-flow transistor logic elements. The representation 25A in FIG. 10 is a basic memory element formed of two inverters $20A_1$ and $20A_2$ (like the inverter 20A) with the output of the inverter $20A_1$ connected as input to the inverter $20A_2$. The representation marked 25B in FIG. 11 is a memory element called a flip-flop; it is made of two NOR-gates $22A_1$ and $22A_2$ (like the NOR-gate 22), the output of the NOR-gate $22A_1$ being connected as one input to the NOR-gate $22A_2$ and the output of NOR-gate $22A_2$ being connected as one input to NOR-gate $22A_1$. The element 25A is merely a bistable logic element, whereas the flip-flop 25B is a bistable logic element which can be set or reset by appropriate signals applied to its inputs 14J and 14H. The outputs of the flip-flop 25B are similar to those of conventional flip-flops similarly constituted from NOR gates except for the effect of $t_{on}$. When both the inputs 14J and 14H in FIG. 11 are LO, the state with one of the outputs 15D and 15E HI and the other LO is retained indefinitely. A HI input applied to the input 14J with input 14H LO forces (after a time $t_{on}$ for the gate $22A_1$) the output 15D LO and (after a time $t_{off}$ for the gate $22A_1$) the output 15E HI. A HI input applied to the input 14H with the input 14J LO forces (after a time $t_{on}$ for the gate $22A_2$), the output 15E LO and (after a time $t_{off}$ for the gate $22A_1$) the output 15D HI. Because of the TURN-ON time, the flip-flop 25B can be constituted to perform a time discrimination function as well as a memory function. For example, if a HI voltage is applied to the input 14J for too short a time to permit TURN-ON, the flip-flop will not be forced into the state with the output 15D LO. Thus, flip-flops constituted of charge-flow transistor logic elements can combine logic functions with memory functions.

There now follows a description of a variety of oscillator circuits that are formed from a plurality of the logic elements either of FIG. 3, FIG. 4, or FIG. 6. The arrangement in FIG. 9 is a ring oscillator 24 formed of an inverter 20A, like the inverter of FIG. 3, and an even number of further inverters $20C_1$, $20C_2$, and $20C_3$ . . . $20C_N$. The inverters $20C_1$ . . . $20C_N$ may be like the charge-flow transistor inverter 20A, and for some uses must be, but there are situations in which inverters $20C_1$ . . . $20C_N$ need not be charge-flow transistor inverters. The ring oscillator 24 exhibits periodic oscillation with a period and/or duty cycle (the duty cycle is usually defined as that fraction of the period during which a given signal is HI) that depends on the TURN-ON and TURN-OFF times of all the inverters in the ring. In conventional logic, where the propagation delays $t_{on}$ and $t_{off}$ are comparable to one another and are roughly equal from one inverter to another, a ring oscillator is formed of an odd number N of nominally identical inverters or oscillators with a period equal to N propagation delays. In the present invention, the period depends both on $t_{on}$ and $t_{off}$ of the at least one charge-flow transistor inverter 20A in the ring, but the period is dominated by $t_{on}$. Hence, the oscillation period of the ring oscillator 24 can depend on a property of the environment through the dependence of $t_{on}$ on that property. Further, if more than one inverter in the ring is a charge-flow transistor inverter, the period (which depends on both $t_{on}$ times) will exhibit a dependence on a property or properties of the environment that combine the dependence of the respective $t_{on}$ times on that property or properties. The present inventor has tested a variety of ring oscillator circuits like 24, and has achieved oscillations in circuits comprising as few as five of the previously described charge-flow transistor inverters incorporating the humidity-sensitive polymer poly(p-aminophenylacetylene). In another embodiment of this invention, a ring oscillator comprising nine of the previously described charge-flow transistor inverters incorporating humidity-sensitive polymer poly(p-aminophenylacetylene) was found to oscillate with a period of 50 milliseconds in normal laboratory ambient of 46% relative humidity, this period decreasing to less than 25 milliseconds when bursts of more humid air (breath) were directed at the charge-flow transistors.

The circuitry labeled 28 in FIG. 12 is an oscillator consisting of two inverters 20A' and 20B' (like the inverter 20A) interconnected with a flip-flop circuit 25C, an example of which is shown in FIG. 12 and includes two NOR gates $22D_1$ and $22D_2$ (which may be like NOR-gate 22B, but may be conventional NOR gates) and two inverters $20D_1$ and $20D_2$ (which may be like the inverter 20A, but may be conventional inverters). The oscillator 28 has two outputs 15F and 15G which are respectively the outputs of the inverters 20A' and 20B' and which are also respectively inputs 27A and 27B to the flip-flop 25C. Flip-flop outputs 27C and 27D are respectively inputs to the inverters 20A' and 20B'. Operation of this oscillator is described assuming the flip-flop 25C is constituted of conventional elements that change state in a time short compared with $t_{on-A}$ for the inverter 20A' and $t_{on-B}$ for the inverter 20B'. A typical half-cycle begins just as the output 15G goes LO (at which instant the output 27D has been HI for a preceding interval, the output 27C has been LO, and the output 15F has been HI). The LO signal on the output 15G (and hence also on the input 27B) causes the input 27F to go HI which, in turn, as in the previous description of the flip-flop 25B, causes the output 27D to become LO and the output 27C to become HI. This causes the inverter 20B' to TURN OFF quickly (i.e., in time $t_{off}$). However, the inverter 20A' does not TURN ON until after a time $t_{on-A}$ for the inverter 20A'. Once TURN-ON of the inverter in 20A' occurs sending the output 15F low, the state corresponding to the start of the alternate half-cycle is reached. The LO signal on the output 15F and the input 27A sends the input 27E HI which sends the output 27C LO and the output 27D HI, turning the inverter 20A' OFF rapidly, and turning the inverter 20B' ON only after time $t_{on-B}$ for the inverter 20B'. In the oscillator 28, assuming that $t_{on-A}$ and $t_{on-B}$ are much longer than all other propagation delays, the period of oscillation is essentially equal to $t_{on-A}+t_{on-B}$, and the duty cycle expressed as a percent is equal to $[100/(1+(t_{on-A}/t_{on-B}))]$. If the inverters 20A' and 20B' are identical, the duty cycle is exactly 50% and the period is equal to $2t_{on}$. If, on the other hand, the inverters 20A' and 20B' are not identical, both the period and duty cycle will vary if either $t_{on-A}$ or $t_{on-B}$ varies, for example, in response to a change in environment.

FIG. 13 shows at 29 one actual circuit realization of the oscillator 28 of FIG. 12. Transistor 100' and load resistor 12A$_1$ in FIG. 13 correspond to the inverter 20A' in FIG. 12 and transistor 100" and load resistor 12A$_2$ correspond to the inverter 20B'. Transistor 102A and load resistor 12A$_3$ correspond to the inverter 20D$_1$, and transistor 102F and load resistor 12A$_6$ correspond to the inverter 20D$_2$. Transistors 102B and 102C together with load element 12A$_4$ constitute NOR-gate 22D$_1$ and transistors 102D and 102E together with load resistor 12A$_5$ constitute NOR-gate 22D$_2$. The present inventor has tested a variety of oscillator circuits like 29, incorporating conventional logic for all but the two charge-flow transistor inverter circuits. In one such circuit in which charge-flow transistors incorporating the humidity sensitive polymer poly(p-aminophenylacetylene) were used, oscillation periods of 97 milliseconds and 50% duty cycles were achieved in normal laboratory ambient (48% relative humidity). In another such circuit, using a pair of charge-flow transistors with large $t_{on}$ values, and operating the circuit in a temperature and humidity-controlled environment, a nearly linear variation in period from 5.4 seconds at 5% relative humidity to 0.77 seconds at 58% relative humidity was observed. Thus, the period of oscillation serves to measure relative humidity.

An important feature of oscillator circuits like 28 is now explained using oscillator 29 of FIG. 13 as an example. If load resistors 12A$_4$ and 12A$_5$ are selected to be not equal to one another, and assuming that transistors 102A . . . 102F are nominally identical, then, except during the short intervals when change-of-state is taking place, the total current drawn by the oscillator depends on whether transistor 102C is ON or transistor 102D is ON (the circuit configuration prevents both being ON simultaneously and also prevents neither being ON). This feature can be exploited for remote two-wire sensing, as shown at 30 in FIG. 14. The power supply 18 in FIG. 14 and a current monitor 17 (which can be a microammeter for example, or a current-sensing resistor) are connected to the oscillator, again marked 29, at terminals 13A and 13B through a wire pair comprising wires 16A and 16B. Because of the different currents drawn by the oscillator in the two flip-flop states, it is possible to monitor the current with the monitor 17 and thereby obtain at a remote location the same information on oscillator period and duty cycle that can be obtained from the outputs of the oscillator 29.

Figure 16:
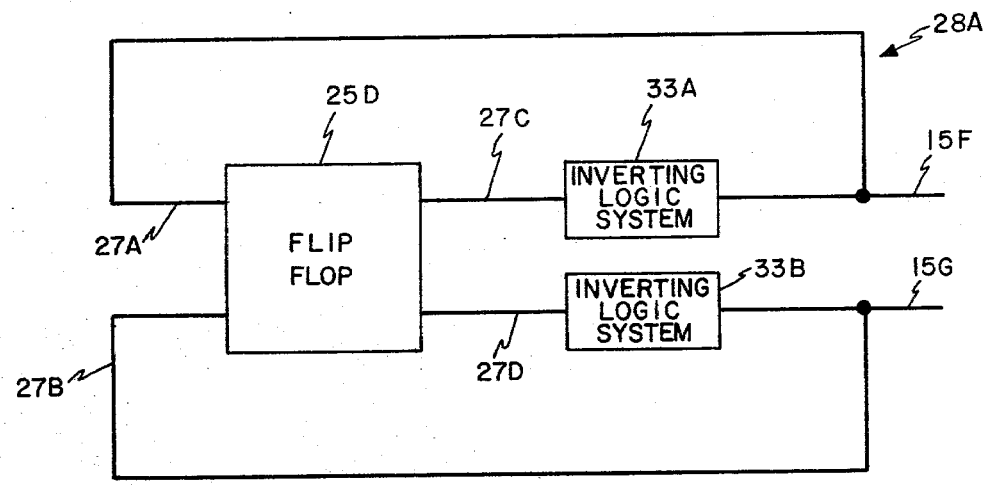
FIG. 16 is a schematic representation of a general oscillator structure comprising a flip-flop memory element and two inverting logic systems.
Figure 17A:
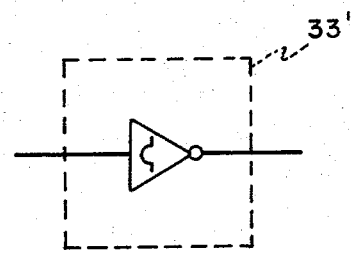
FIGS. 17A–17D are schematic representations of different types of inverting logic systems that can be employed in the oscillator of FIG. 16.
Figure 17B:
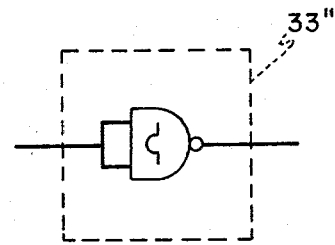
Figure 17C:
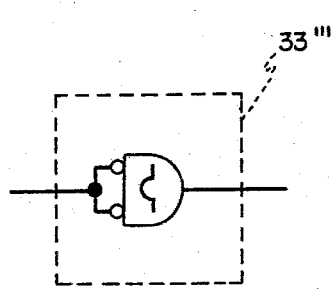
Figure 17D:
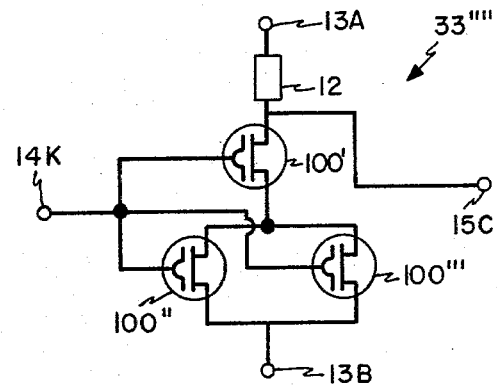

A more general case of the oscillator 28 of FIG. 12 is shown at 28A in FIG. 16 wherein most of the labeled circuit elements are given the same or similar labels to those of FIG. 12. The oscillator 28A consists of a flip-flop 25D (which may be like the flip-flop 25C of FIG. 12) and inverting logic systems 33A and 33B whose outputs are the outputs 15F and 15G of oscillator 28A and also are connected as inputs to the flip-flop 25D. The inverting logic systems 33A and 33B may take any of the forms in FIGS. 17A–17D which are respectively an inverter 33' (e.g., like the inverter 20 of FIG. 3), a NAND-gate 33'' (e.g., like the NAND-gate 21 of FIG. 4, but connected to perform an inverting function), a NOR-gate 33''' (e.g., like the NOR-gate 22 of FIG. 6, but connected to perform an inverting function), and a complex logic unit 33'''' formed of a NAND-gate and a NOR-gate connected to perform an inverting logic function.

The oscillator 28A combines the features of the oscillator 28 of FIG. 12 with the signal-processing capability of the logic elements and logic systems of FIGS. 3, 4, 6, and 8. The flip-flop 25D is connected to inverting logic systems 33A and 33B, these inverting logic systems having the same overall logic function as a simple inverter. However, by employing logic elements and logic systems of the present invention, it is possible to have these inverting logic systems perform signal-processing within the same oscillator circuit that is being used to provide information on $t_{on}$ of the inverting logic systems. As with the oscillator 28 of FIG. 12, the oscillator circuit 28A of FIG. 16 oscillates with a period that is about equal to $t_{on-A}+t_{on-B}$, where $t_{on-A}$ is the TURN-ON time for inverting logic system 33A and $t_{on-B}$ is the TURN-ON time for inverting logic system 33B. Examples of these inverting logic systems are shown in FIGS. 17A–17D. One possible case is that of the simple inverter, already shown in FIG. 12 as part of the oscillator, and shown as 33' in FIG. 17A. Additional possibilities are shown at 33'', 33''', and 33'''' of FIGS. 17B–17D respectively. At 33'', the NAND logic element of FIG. 4 is used with both inputs connected together to provide an overall inverter function; however, this inverter comprises two charge-flow transistors, each with its own $t_{on}$. As described earlier, the $t_{on}$ for the NAND element is the longer of the two $t_{on}$ values for the two charge-flow transistors. Hence, an oscillator incorporating NAND logic elements connected as inverters will oscillate with a period that is determined by the longer of the $t_{on}$ times in the NAND element. Similarly, the NOR element of FIG. 6 can be connected to provide an overall inverter function, as shown at 33''' in FIG. 17C. In this case, the $t_{on}$ for the inverter is the shorter of the $t_{on}$ times for the two charge-flow transistors in the NOR element. Finally, complex logic units, as described with reference to FIG. 8, can be connected to provide an overall inverter function, as shown at 33"" in FIG. 17D; input to the unit 33"" is at 14K and its output is 15C.

In working with oscillator circuits such as 24, 28 and 29, the present inventor has found in some cases a tendency for drift in frequency (or, equivalently, in period) which can be attributed to charge storage in the thin-film material of the charge-flow transistor. The charge-storage effect has been previously described in the application for Letters Patent, Ser. No. 790,631. The effect of charge-storage is to reduce $t_{on}$ as the long-term average of the input voltage increases. Even in oscillator 28, which for nominally identical inverters 20A' and 20B' should yield a constant 50% duty cycle, and hence a stable average input signal for each inverter, after times on the order of 15 minutes, non-50% duty cycles begin to appear. This is attributed to slight inequivalence between the $t_{on}$ characteristics of nominally identical transistors.

An oscillator circuit 31 that automatically compensates for such charge-storage effects on $t_{on}$, period, and duty cycle, is illustrated in FIG. 15. The oscillator comprises four inverters 20A₁, 20A₂, 20A₃, and 20A₄ and two flip-flops 25B₁ (having inputs 27A and 27B and outputs 27C and 27D as in flip-flops 25C of FIG. 12, the outputs 27C and 27D also serving as inputs to inverters 20A₁ and 20A₂, respectively, and the inputs 27A and 27B being connected to the outputs of inverters 20A₃ and 20A₄, respectively) and 25B₂ (having, correspondingly, inputs 27A' and 27B' and outputs 27C' and 27D', the outputs serving, respectively, as inputs to inverters 20A₃ and 20A₄, and the inputs being connected, respectively, to the outputs of inverters 20A₁ and 20A₂). The inverters 20A₁ and 20A₄ are nominally identical to one another, and 20A₂ and 20A₃ are nominally identical to one another. If the average value of input 27C to the inverter 20A₁ increases, producing a decrease in $t_{on}$ for the inverter 20A₁, then the average value of input 27C' to the inverter 20A₄ decreases, producing a compensating increase in $t_{on}$ for the inverter 20A₄ and tending thereby to reduce the average value of the input 27C. Thus, the oscillator 31 has a stable duty cycle (that depends on the relative sizes of $t_{on}$ for inverters 20A₁ and 20A₂) and a period that is the sum of all four $t_{on}$ values.

Further modifications of the present invention will occur to persons skilled in the art and all such modifications are deemed to be within the scope of the invention as defined by the appended claims.

What is claimed is:

1. An oscillator that comprises a flip-flop and two inverting logic systems interconnected and acting in combination, each inverting logic system including, in combination, a charge-flow transistor comprising a semiconductor substrate, a drain region, a source region, a gate insulator, a gapped-gate electrode and a thin-film material having some electrical conductance disposed in the gap of the gapped gate electrode, and a load element connected to either the source or the drain of the charge-flow transistor, the TURN-ON time $t_{on}$ of each inverting logic system being determined primarily by the conductance of the thin-film material of the charge-flow transistor of the particular inverter, the time $t_{on}$ of each inverting logic system being much greater than the TURN-OFF time $t_{off}$ thereof, said oscillator having two outputs that are outputs of the two inverting logic systems, the two outputs also being connected as two inputs to the flip-flop which has two outputs that are connected as inputs to the two inverting logic systems, said flip-flop being operable in response to the inputs thereto from the two inverting logic systems each of whose TURN-ON time $t_{on}$ is much greater than its TURN-OFF time $t_{off}$ to effect periodic TURN-ON and TURN-OFF of said two inverting logic systems to achieve oscillation of the oscillator with the period of oscillation being dominated by said time $t_{on}$ of both inverting logic systems.

2. An oscillator as claimed in claim 1 in which the electrical conductance of the thin-film material of at least one charge-flow transistor of the two inverting systems is sensitive to a property of the environment about the oscillator such that the time $t_{on}$ of said at least one transistor is affected by changes in said property to affect the frequency of oscillation and the duty cycle of the oscillator as a function of said property.

3. An oscillator as claimed in claim 2 wherein the thin-film material in the charge-flow transistor of one inverting logic system of the two inverting logic systems differs from the thin-film material in the charge-flow transistor of the other inverting logic system of the two inverting logic systems.

4. An oscillator as claimed in claim 2 wherein the thin-film material in the charge-flow transistor of one inverting logic system of the two inverting logic systems is the same as the thin-film material in the charge flow transistor of the other inverting logic system of the two inverting logic systems.

5. An oscillator as claimed in claim 2 wherein variations in the time $t_{on}$ of one inverting logic system of the two inverting logic systems differs from the time $t_{on}$ of the other inverting logic system as a function of said property.

6. An oscillator as claimed in claim 2 wherein said two inverting logic systems are inverters.

7. An oscillator as claimed in claim 2 wherein at least one of the two inverting logic systems comprises a two-input NAND-gate connected to perform an inverting function.

8. An oscillator as claimed in claim 7 in which the two input NAND-gate comprises two charge-flow transistors.

9. An oscillator as claimed in claim 2 wherein at least one of the two inverting logic systems comprises a two-input NOR-gate connected to perform an inverting function.

10. An oscillator as claimed in claim 9 in which the NOR-gate comprises two charge-flow transistors.

11. An oscillator as claimed in claim 1 wherein at least one of the two inverting logic systems comprises a plurality of charge-flow transistors.

12. An oscillator as claimed in claim 2 wherein at least one of the two inverting logic systems is a complex logic unit formed of a NAND-gate and a NOR-gate connected to perform an inverting logic function.

13. An oscillator that includes, in combination: at least one logic element, having an input and an output, and electrical circuit means having an input and an output, the output of the logic element being connected to the input of the electrical circuit means and the output of the electrical circuit means being connected to the input of the logic element, the electrical circuit means being operable to effect TURN-ON and TURN-OFF of the logic element to provide periodic oscillations; said logic element comprising the combination of a load element and a charge-flow transistor, the charge flow transistor comprising a semiconductor substrate, a drain region, a source region, a gate insulator, a gapped gate electrode, a gap material having some electrical conductance disposed in the gap of the gapped gate electrode and electrically connected thereto, said gate insulator being sandwiched between the conductive fingers and the substrate and between the gap material and the substrate, the load element being connected to one of the source region and the drain region of the charge-flow transistor, the TURN-ON time of the logic element being determined primarily by the conductance of the gap material, the input of the logic element being the gate electrode of the charge-flow transistor and the output of the logic element being the one of the source and drain thereof to which the load element is connected.

14. An oscillator as claimed in claim 13 in which the gap material of the charge-flow transistor in said at least one logic element is sensitive to an environmental property which affects the TURN-ON time of the logic element.

15. An oscillator as claimed in claim 13 comprising a plurality of logic elements, each comprising a charge-flow transistor and in which the gap material of the charge-flow transistor of each logic element is an organic polymer.

16. A ring oscillator comprising an odd number greater than one of logic elements and in which the output of each such logic element is connected to the input of another logic element to form a ring connection, each said logic element comprising: a charge-flow transistor comprising a semiconductor substrate, a drain region, a source region, a gate insulator, a gapped gate electrode, and a thin-film material having some electrical conductance disposed in the gap of the gapped gate electrode, and a load element connected to one of the source region and drain region of the charge-flow transistor, the TURN-ON time of logic element being determined primarily by the conductance of said thin-film material, the input to the logic element being the gate electrode of the charge-flow transistor, the output thereof being the one of the source and drain thereof to which the load element is connected.

17. A sensor circuit comprising a ring oscillator as claimed in claim 16 and in which the material in said gap of at least one of the charge-flow transistors is sensitive to a property of the environment within which the charge-flow transistor is located and in which the TURN-ON time of at least one of the charge-flow transistors is modified by a change in said property.

18. An oscillator comprising two logic elements and a flip-flop, in which each of the two logic elements functions as a delayed inverter, the outputs of the two logic elements being connected as inputs to the flip-flop such that TURN-ON of one logic element of the two logic elements causes a change of state of the flip-flop, said change of state serving to initiate TURN-ON of the second logic element of the two logic elements, said flip-flop having two outputs that are connected as inputs to the two logic elements, each logic element comprising a load element and a charge-flow transistor, said charge-flow transistor comprising a semiconductor substrate, a drain region, a source region, a gate insulator, a gapped gate electrode, a gap material having some electrical conductance disposed in the gap of the gapped gate electrode, said load element being connected to one of the source region and the drain region of the charge-flow transistor, the TURN-ON time of the logic element being determined primarily by the conductance of said gap material, the input of the logic element being the gate electrode of the charge-flow transistor and the output thereof being the one of the source and drain thereof to which the load element is connected.

19. An oscillator comprising four logic elements, each logic element of the four functioning as an inverter, and a pair of flip-flops, a first pair of the four inverters being connected with the outputs thereof connected as inputs to one flip-flop of the pair of flip-flops, the outputs of said one flip-flop being connected as inputs to the second pair of the four inverters, the outputs of said second pair being connected as inputs to the other flip-flop of the pair of flip-flops, the outputs of the said other flip-flop being connected as inputs to the first pair of inverters so that the duty cycle of the oscillator is stable, each logic element of the four logic elements comprising a load element and a charge-flow transistor interconnected, said charge-flow transistor comprising a semiconductor substrate, a drain region, a source region, a gate insulator, a gapped gate electrode, a gap material having some electrical conductance disposed in the gap of the gapped gate electrode, said load element being connected to one of the source region and the drain region of the charge-flow transistor, the TURN-ON time of the logic element being determined primarily by the conductance of said gap material, the input of each logic element being the gate electrode of the charge-flow transistor and the output thereof being the one of the source and drain thereof to which the load element is connected.

20. An oscillator comprising a first pair of logic elements and a second pair of logic elements, each logic element comprising a charge-flow transistor comprising a semiconductor substrate, a drain region, a source region, a gate insulator, a gapped gate electrode, and a thin-film material having some electrical conductance disposed in the gap of the gapped gate electrode, and a load element connected to one of the source region and drain region of the charge-flow transistor, the TURN-ON time of the logic element being determined primarily by the conductance of said thin-film material, the input to the logic element being the gate electrode of the charge-flow transistor and the output thereof being the one of the source and drain thereof to which the load element is connected, said oscillator further including a first flip-flop and a second flip-flop, each flip-flop having two inputs and two outputs, the outputs of the first flip-flop being connected as inputs to the first pair of logic elements whose individual outputs are connected as inputs to the second flip-flop whose outputs are connected as inputs to the second pair of logic elements whose individual outputs are connected as inputs to the first flip-flop.

21. An oscillator as claimed in claim 20 wherein the logic elements and flip-flops are chosen to have appropriate characteristics to achieve frequency drift compensation.

22. An oscillator that includes, in combination: at least one logic element, said at least one logic element comprising a charge-flow transistor that comprises a semiconductor substrate, a drain region, a source region, a gate insulator, a gapped gate electrode, a gap material having some electrical conductance disposed in the gap of the gapped gate electrode, and an electrical load element connected to one of the source region and the drain region of the charge-flow transistor, said at least one logic element having an input and an output; and electrical circuit means connected to receive as input thereto the output of the logic element, said electrical circuit means having an output fed back as input to the logic element and being operable in response to the input of the electrical circuit means to effect periodic TURN-ON and TURN-OFF of the logic element.

23. An oscillator as claimed in claim 22 in which the gap material of the charge-flow transistor in said at least one logic element is sensitive to an environmental property which affects the TURN-ON time of the logic element.

24. An oscillator as claimed in claim 23 comprising a plurality of logic elements, each comprising a charge-flow transistor, and in which the gap material of the charge-flow transistor of each logic element is sensitive to an environmental property which affects the TURN-ON time of each logic element.

25. An oscillator as claimed in claim 24 wherein the material in the gap of each of the charge-flow transistors is sensitive to the same property of the environment.

26. An oscillator as claimed in claim 24 wherein the material of the gap of one transistor of the plurality differs from the material in the gap of at least one other transistor of the plurality so that said one transistor is sensitive to a different property of the environment than is said at least one other transistor.

27. An oscillator as claimed in claim 22 wherein said electrical circuit means comprises a bistable element whose output is fed back as input to the logic element.

28. An oscillator as claimed in claim 27 wherein the bistable element is a flip-flop.

29. An oscillator as claimed in claim 22 in which the TURN-ON time of the logic element is $t_{on}$ and the TURN-OFF time of the logic element is $t_{off}$, the frequency of oscillation of the oscillator being determined primarily by the said TURN-ON time $t_{on}$, the time $t_{on}$ being determined primarily by the conductance of the gap material, the time $t_{on}$ being much greater than the time $t_{off}$.

30. An oscillator as claimed in claim 22 in which the TURN-ON time is $t_{on}$ and the TURN-OFF time is $t_{off}$ and in which said gap material exhibits two modes of conduction and is subject to charge storage which affects the TURN-ON time $t_{on}$ of the charge-flow transistor.

31. An oscillator as claimed in claim 30 wherein the electrical circuit means comprises a bistable element.

32. An oscillator as claimed in claim 31 where the effect of said charge storage is to modify the period of oscillation and which includes means to effect automatic compensation to maintain stable oscillation.

33. An oscillation as claimed in claim 30 in which $t_{on} >> t_{off}$, in which the time $t_{on}$ is determined primarily by the electrical properties of the gap material, in which the period of oscillation of the oscillator is dominated by the time $t_{on}$, and in which the electrical circuit means is adapted to take into consideration any charge storage in the gap material and to achieve stable oscillations despite changes in said charge storage which would otherwise adversely affect such stable oscillations.

34. An oscillator as claimed in claim 22 in which the period of oscillation is dominated by the conductance of the gap material and in which said electrical circuit means is adapted to take into consideration any charge storage in gap material and to effect stable oscillations despite changes in said charge storage which would otherwise deleteriously affect oscillation.

35. A ring oscillator comprising at least one logic element that includes the combination of a load element and a charge-flow transistor comprising a semiconductor substrate, a drain region, a source region, a gate insulator, a gapped gate electrode, and a thin-film material having some electrical conductance disposed in the gap of the gapped gate electrode, said load element being connected to one of the source region and drain region of the charge-flow transistor, which logic element functions as an inverter, said ring oscillator further including an even number of additional inverters.

36. A ring oscillator as claimed in claim 35 in which said even number is at least four.

37. A sensor circuit comprising a ring oscillator as claimed in claim 36 in which the material in said gap of at least one of the charge-flow transistors is sensitive to a property of the environment within which the charge-flow transistor is located and in which the TURN-ON time of at least one of the charge-flow transistors is modified by a change in said property.

38. A ring oscillator comprising an odd number greater than one of logic elements, each logic element comprising the combination of a load element and a charge-flow transistor comprising a semiconductor substrate, a drain region, a source region, a gate insulator, a gapped gate electrode, and a thin-film material having some electrical conductance disposed in the gap of the gapped gate electrode, said load element being connected to one of the source region and drain region of the charge-flow transistor, the output of each such logic element being connected to the input of another logic element to form a ring connection.

39. A sensor circuit comprising a ring oscillator as claimed in claim 38 in which the material in said gap of at least one of the charge-flow transistors is sensitive to a property of the environment within which the charge-flow transistor is located and in which the TURN-ON time of at least one of the charge-flow transistors is modified by a change in said property.

40. A sensor circuit comprising a ring oscillator as claimed in claim 38 and in which the current drawn by one element when turned-on differs from the current drawn by the other element or elements of the circuit, the charge-flow transistor of at least one of the inverters having a material in said gap having an electrical conductance that is sensitive to a property of the environment within which said at least one of the inverters is located.

41. A sensor system comprising a sensor circuit as claimed in claim 40 that includes a power supply and monitoring means to monitor the total current drawn from the power supply by said sensor circuit.

42. An oscillator that comprises two logic elements and that further includes a flip-flop, each logic element of the two logic elements having an input and an output, the flip-flop having two inputs and two outputs, the outputs of the two logic elements being connected to respective inputs of the flip-flop, the two outputs of the flip-flop being connected to respective inputs of the two logic elements, each said logic element of the two logic elements comprising a load element and a charge-flow transistor, said charge-flow transistor comprising a semiconductor substrate, a drain region, a source region, a gate insulator, a gapped gate electrode and a thin-film material having some electrical conductance disposed in the gap of the gapped gate electrode, said load element being connected to one of the source region and the drain region of the charge-flow transistor, the thin-film material of the charge-flow transistor of one of the two logic elements having an electrical conductance that is sensitive to a property of the environment within which the charge-flow transistor is located, the TURN-ON time of the charge-flow transistor whose thin-film material is sensitive to a property of the environment being modified by a change in said property.

43. An oscillator as claimed in claim 42 in which each of the two logic elements functions as a delayed inverter in which interconnection of the two logic elements and the flip-flop is such that TURN-ON of one logic element of the two logic elements causes a change of state of the flip-flop, said change of state serving to initiate TURN-ON of the second logic element of the two logic elements.

44. A sensor system comprising a plurality of logic elements and bistable means connected as an oscillator, each logic element comprising the combination of a load element and a charge-flow transistor comprising a semiconductor substrate, a drain region, a source region, a gate insulator, a gapped gate electrode, and a thin-film material having some electrical conductance disposed in the gap of the gapped gate electrode, said load element being connected to one of the source region and drain region of the charge-flow transistor, each logic element having an input and an output, the bistable means having two inputs and two outputs, the outputs of the logic elements being connected as inputs to the bistable means whose outputs are connected as inputs to the logic elements, a power supply connected to energize the oscillator, and monitoring means connected to monitor the period and duty cycle of the oscillator, the oscillator being disposed at a remote location from the power supply and the monitoring means, and the electrical connection between the power supply and monitoring means and the oscillator being a single pair of wires.

45. An oscillator that comprises a plurality of logic elements, each logic element having, in combination: a charge-flow transistor comprising a semiconductor substrate, a drain region, a source region, a gapped gate electrode comprising a pair of fingers with a gap between the fingers, a gap material having some electrical conductance disposed in said gap, the conductance of said gap material being much less than the conductance of the conductive fingers, a gate insulator sandwiched between the conductive fingers and the substrate and between the gap material and the substrate, said gap material being electrically connected with the gapped gate electrode to permit charge flow in the gap material to control current flow in the substrate adjacent the gate insulator, the TURN-ON time $t_{on}$ of the logic element being determined primarily by the electrical properties of the gap material, the time $t_{on}$ being much greater than the TURN-OFF time $t_{off}$ thereof, and a load element connected to one of the source region and the drain region of the charge-flow transistor; and electric-circuit means connected to receive as inputs thereto outputs from the plurality of logic elements and to provide outputs that are fed back as inputs to the plurality of logic elements.

46. An oscillator that comprises a plurality of logic elements, each logic element having, in combination, a charge-flow transistor comprising a semiconductor substrate, a drain region, a source region, a gapped gate electrode comprising a pair of conductive fingers with a gap between the fingers, a gap material having some electrical conductance disposed in said gap, the bulk conductance of the gap material differing substantially from the surface conductance thereof which causes charge storage to occur in the gap material of the charge-flow transistor during operation of the oscillator, the conductance of said gap material being much less than the conductance of the conductive fingers, a gate insulator sandwiched between the gap material and the substrate, said gap material being electrically connected with the gapped gate electrode to permit charge flow in the gap material to control current flow in the substrate adjacent the gate insulator, the TURN-ON time $t_{on}$ of the logic element being determined primarily by the electrical properties of the gap material, and a load element connected to one of the source region and the drain region of the charge-flow transistor, said oscillator being adapted to oscillate despite the presence of said charge storage; and bistable means connected to receive outputs from the plurality of logic elements and to provide inputs to the logic elements to effect oscillations whose periods are dominated by the TURN-ON time $t_{on}$ of the plurality of logic elements.

47. An oscillator that comprises, in combination, an inverter logic circuit comprising the combination of a charge-flow transistor and a load element, and electrical circuit means connected to receive as input the output of the logic element and to provide an output that is fed back as input to the logic element, said charge-flow transistor comprising a semiconductor substrate, a drain region, a source region, a gapped gate electrode comprising a pair of conductive fingers with a gap between the fingers, a gap material having some electrical conductance disposed in said gap, the conductance of said gap material being much less than the conductance of the conductive fingers, a gate insulator sandwiched between the gap material and the substrate, said electrical circuit means being operable to effect periodic TURN-ON and TURN-OFF of the logic element.

48. An oscillator that comprises, in combination, an inverter logic element comprising the combination of a charge-flow transistor and a load element; and bistable means connected to receive as input the output of the logic element and to provide an output which is fed back as input to the logic element, said bistable means being operable in response to the input thereto from the inverter logic element to effect periodic TURN-ON and TURN-OFF of the logic element.

* * * * *